United States Patent [19]
Snyder et al.

[11] Patent Number: 5,439,938
[45] Date of Patent: Aug. 8, 1995

[54] TREATMENTS FOR MALE SEXUAL DYSFUNCTION

[75] Inventors: Solomon H. Snyder; Arthur L. Burnett, both of Baltimore; Charles J. Lowenstein, Tacoma Park; David S. Bredt; Thomas S. K. Chang, both of Baltimore, all of Md.

[73] Assignee: The Johns Hopkins University, Baltimore, Md.

[21] Appl. No.: 43,821

[22] Filed: Apr. 7, 1993

[51] Int. Cl.⁶ .......................................... A61K 31/195
[52] U.S. Cl. ................................................. 514/565
[58] Field of Search ............... 514/535, 561, 565, 742, 514/236.2; 424/449

[56] References Cited

U.S. PATENT DOCUMENTS

| | | | |
|---|---|---|---|
| 4,127,118 | 11/1978 | Latorre | 128/79 |
| 4,801,587 | 1/1989 | Voss et al. | 514/248 |
| 4,829,991 | 5/1989 | Boeck | 128/79 |
| 5,059,603 | 10/1992 | Rubin | 514/264 |
| 5,155,109 | 10/1992 | Schonafinger et al. | 514/252 |
| 5,187,305 | 2/1993 | Thompson et al. | 560/145 |
| 5,225,440 | 7/1993 | London et al. | 514/535 |
| 5,242,391 | 9/1993 | Place et al. | 604/60 |

OTHER PUBLICATIONS

Burnett, et al., "Nitric Oxide: A Physiologic Mediator of Penile Erection", *Science* 257:401–403 (1992).
Gillespie et al., "The Effect of Arginine and L-N Monomethyl Arginine on the Response of the Bovine Retractor Penis to Simulation of its NANC Nerves", *Br. J. Phar.* 97:453P (1989).
Holmquist, et al., "Effects of the Nitric Oxide Synthase Inhibitor N$^G$-Nitro-L-Arginine on the Erectile Response to Cavernous Nerve Stimulation in the Rabbit", *Acta Physiol. Scand.* 143:299–304 (1991).
Holmquist, et al., "L-N$^G$-Nitro Arginine Inhibits Non-Adrenergic, Non-Cholinergic Relaxation of Human Isolated Corpus Cavernosum", *Acta Physiol. Scand.*, 141:441–443 (1991).
Ignarro, et al., "Neurotransmitter Identity Doubt," *Nature*, 347:131–132 (1990).
Ignarro, et al. "Nitric Oxide and Cyclic GMP Formation Upon Electrical Field Stimulation Cause Relaxation of Corpus Cavernosum Smooth Muscle," *Biochem. Biophys. Res. Comm.*, 170(2):843–850 (1990).
Kim, et al., "A Nitric Oxide-like Factor Mediates Nonadrenergic-Noncholigenergic Neurogenic Relaxation of Penile Corpus Cavernosum Smooth Muscle," *J. Clin. Invest.* 88:112–118 (1991).
Pickard, et al., "The Effect of Inhibitors of Nitric Oxide Biosynthesis and Cyclic GMP Formation on Nerve--Evoked Relaxation of Human Cavernosal Smooth Muscle," *Br. J. Pharmacol.*, 104:755–759 (1991).
Rajfer, et al., "Nitric Oxide as a Mediator of Relaxation of the Corpus Cavernosum in Response to Non-Adrenergic, Non-cholinergic Neutrotransmission," *New Engl. J. Med.*, 326(2):90–94 (1992).
Sjöstrand, et al., "The Effects of L-arginine and N$^G$-Monomethyl L-arginine on the Inhibitory Neurotransmission of the Human Corpus Cavernosum Penis," *Acta Physiol. Scand.*, 104:297–298 (1990).
Stroh, "The Root of Importance, Does Nitric Oxide Hold the Key?", *Science News*, 142(1):10–11 (1992).
Martindale, The Extra Pharmacopoeia, 28th edition (1982) p. 1729.
CRC "Controlled Drug Delivery", vol. II (1983) pp. 73–76.

*Primary Examiner*—Raymond Henley, III
*Attorney, Agent, or Firm*—Banner, Birch, McKie & Beckett

[57] ABSTRACT

Methods and devices are taught for regulating penile erection and urethral function. Inhibitors of nitric oxide synthase and precursors of nitric oxide are applied to relax or contract the muscles of the corpus cavernosum and the urethra.

33 Claims, 1 Drawing Sheet

5,439,938

TREATMENTS FOR MALE SEXUAL DYSFUNCTION

TECHNICAL FIELD OF THE INVENTION

This invention relates to the physiology of the male reproductive organ. Specifically it relates to the neuronal messenger which initiates erection.

BACKGROUND OF THE INVENTION

Nitric oxide (NO) mediates bactericidal and tumoricidal actions of macrophages (J. B. Hibbs et al., *J. Immunol.* 138:550 (1987); J. B. Hibbs et al., *Biochem. Biophys. Res. Commun.* 157:87 (1988); C. F. Nathan et al., *Curr. Opin. Immunol.* 3:65 (1991)) and blood vessel relaxation of endothelial cells (R. F. Furchgott et al., *Nature* 288:373 (1980); S. Moncada et al., *Biochem, Pharmacol.* 38:1709 (1989); R. M. Palmer, et al., *Nature* 327:524 (1987); R. F. Furchgott et al., FASEB J. 3:2007 (1988); L. J. Ignarro, *Annu. Rev. Pharmacol. Toxicol.* 30:535 (1990)). NO also is likely a major neuronal messenger (D. S. Bredt et al., *Neuron* 8:3 (1992); J. Garthwaite, *Trends Neurosci.* 14:60 (1991)). Immunohistochemical studies localize NO synthase (NOS) to neurons in the brain as well as to discrete populations of autonomic nerves in the periphery (D. S. Bredt et al., *Nature* 347:768 (1990)), where NO fulfills most characteristics of a neurotransmitter. For instance, NOS is highly localized to cell bodies and fibers of the myenteric plexus of the gastrointestinal pathway (Bredt, et al., supra; Garthwaite, supra). The non-adrenergic, non-cholinergic relaxation evoked by physiologic stimulation of myenteric plexus neurons is potently and selectively blocked by NOS inhibitors (K. M. Desai et al., *Nature* 351:477 (1991); T. M. Cocks et al., *Naunyn Schmiedebergs Arch. Pharmacol.* 341:364 (1990); A. Tttrup et al., *Am. J. Physiol.* 260:G385 (1991); H. Bult et al., *Nature* 345:346 (1990); J. S. Gillespie et al., *Br. J. Pharmacol.* 98:1080 (1989); M. V. Ramagopal et al., *Euro. J. Pharmacol.* 174:297 (1989); A. Gibson et al., *Br. J. Pharmacol.* 99:602 (1990).

Penile erection is thought to involve parasympathetic, neuronally mediated relaxation of the blood vessels as well as of the trabecular meshwork of smooth muscle comprising the corpora cavernosa (R. Blanco et al., *Am. J. Physiol.* 254:468 (1988)). The neuronal chemical mediator of erection has not been established. Vasoactive intestinal polypeptide (VIP) occurs in limited populations of nerve fibers in the penis (J. M. Polak, *Lancet* 2:217 (1981); E. A. Willis et al., *Life Sci.* 33:383 (1983)), but direct administration of VIP does not fully mimic physiologic erection (E. A. Kiely et al., *Br. J. Urol.* 64:191 (1989); J. B. Roy et al., *J. Urol.* 143:302 (1990); K. P. Juenemann, et al, *J. Urol.* 138:871 (1987); W. D. Steers et al., J. Urol. 132:1048 (1984).). In isolated smooth muscle from the corpus cavernosum of several species, relaxation evoked by electrical field stimulation could be blocked by NOS inhibitors in some studies (R. S. Pickard et al., *Br. J. Pharmacol.* 104:755 (1991); L. J. Ignarro et al., *Biochem. Biophys. Res. Commun.* 170:843 (1990); N. Kim et al., *J. Clin. Invest.* 88:112 (1991); F. Holmquist et al., *Acta Physiol. Scan.* 141:441 (1991); J. Rajfer et al., *New Eng. J. Med.* 326:90 (1992) but not in others (J. S. Gillespie et al., *Br. J. Pharmacol.* 97:453P (1989); N. O. Sjostrand et al., *Acta. Physiol. Scan.* 140:297 (1990). Blockade of relaxation of isolated smooth muscle by NOS inhibitors can establish NO as a mediator of cavernosal muscle relaxation but does not permit conclusions as to whether it is a neuronal, transmitter-like messenger or whether it can mediate a physiologic erection in an intact body. There is a need in the art for methods of inducing erections in males who are now incapable of achieving them. There is also a need in the art for methods of relieving erections which are not associated with sexual arousal or desire.

SUMMARY OF THE INVENTION

It is an object of the invention to provide a method for treating priapism.

It is another object of the invention to provide a method for treating male impotence.

It is yet another object of the invention to provide salves and patches for treating priapism.

These and other objects of the invention are provided by one or more of the embodiments described below. In one embodiment of the invention a method for treating priapism is provided. The method comprises the step of applying to an erect penis an inhibitor of NO synthase in an amount sufficient to cause said penis to become flaccid.

In another embodiment of the invention a method for treating male impotence is provided. The method comprises the step of applying to a flaccid penis a compound which generates NO in an amount sufficient to initiate penile erection.

In yet another embodiment of the invention a salve is provided which is useful for intradermal administration of a drug. The salve comprises a drug which is inhibitory to NO synthase.

In still another embodiment of the invention a patch is provided which is useful for intradermal administration of a drug. The patch comprises a drug which is inhibitory to NO synthase.

The present invention provides the art with new methods and compositions for treating male sexual dysfunction.

BRIEF DESCRIPTION OF THE DRAWINGS

(FIG. 1 C) Duplicate section as (FIG. 1B) which was obtained in an animal one week following bilateral transection of the cavernous nerves. Very faint staining is observed in the adventitia of the major arterial divisions.

(FIG. 1A), (FIG. 1B), (FIG. 1C), and (FIG. 1F) 300 μm, (FIG. 1D) and (FIG. 1E) 1 mm].

DETAILED DESCRIPTION OF THE INVENTION

Figure 1A:
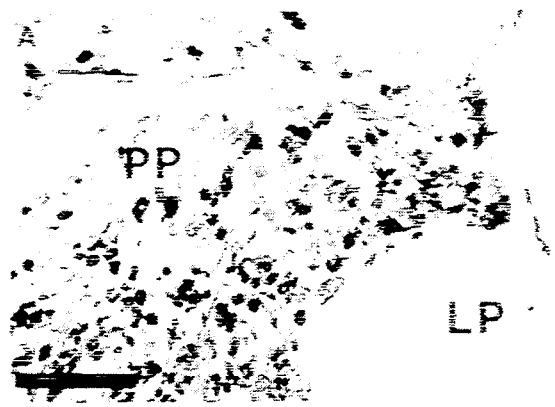
(FIG. 1A) The pelvic plexus (PP) containing neuronal cell bodies adjacent to glands of the lateral prostate (LP).

It is a discovery of the present invention that NO (nitric oxide) is produced in the penile neurons innervating the corpora cavernosa and in the neuronal plexuses in the adventitial layer of penile arteries. Very low doses of NO synthase inhibitors abolish electrophysiologically induced penile erections. These results establish NO as a physiologic mediator of erectile function.

According to the present invention, priapism (a condition of painful, prolonged erections not associated with sexual arousal or desire) can be treated. Priapism occurs in several clinical situations, including as many as 40% of patients with sickle cell anemia. Emond, *Arch. Intern. Med.* 140:1434 (1980). To reduce the erections, NO synthase inhibitors can be administered intravenously, directly injected, or applied topically. While such topical administration may be directly to the skin, it may also be into the urethra. The mucosal lining of the urethra is much more permeable to drugs that the skin and the tough connective tissue layers of the corpora cavernosae. Lotions, cremes, salves, ointments etc. which represent suitable vehicles for topical administration and for retention of activity of the active ingredient, may be applied manually, or in the case of intraurethral application, by means of an injection device. Alternatively, the active ingredient may be administered in a transdermal patch. The active ingredient for reduction of erections can be any compound which effectively inhibits NO synthase. This set includes L-nitroarginine(methyl ester), N-methyl-L-arginine, and amino arginine. Such inhibitors compete for the substrate building site of NOS or bind to other sites on the enzyme. They may be reversible or irreversible inhibitors.

The present invention contemplates the use of any physiologically acceptable inhibitor which inhibits NOS activity. The effectiveness of a compound, and its relative potency as an NOS inhibitor, can be tested and routinely determined by measuring inhibition of NOS activity in vitro by monitoring the conversion of arginine to citrulline by NOS in, for example, cerebellar homogenates. A reduction in citrulline formation indicates inhibitory activity of the compound. The percent reduction in citrulline formation, compared to amount of citrulline formed in the absence of the compound being tested, indicates the potency of the compound as an NOS inhibitor. See Bredt et al., *Proc. Natl. Acad. Sci. USA,* 87:682 (1990).

In addition to nitroarginine, aminoarginine and methylarginine, other inhibitors of NOS have been developed. Inhibitors have been prepared from arginine, nitroarginine and guanidinoalkanoic acids, in which the guanidino group, the amino group, the carboxyl group and the backbone have been systematically altered.

Among the nitroarginine analogs tested, nitroarginine was the most potent inhibitor. In general, the introduction of the nitro group on the guanidine moiety appears to result in selective inhibition of the NOS enzyme. Moreover, it was found that the nature of substituents on the β-amino group seemed to dictate the inhibition potency of the compounds. Whereas a free β-amino group provides good inhibitors, the substitution of the amino group with a bulky protective group, such as benzyloxy, results in total loss of activity. A small substituent, such as a formyl group, appears to be favorable.

In the guanidinoalkanoic acid series, it has been found that 6-guanidinohexanoic acid (6-GHA) and 5-guanidinopentanoic acid (5-GPA) are inactive against the NOS found in brain and peripheral tissues. The nitro analogs of 6-GHA and 5-GPA were found to be generally inactive, as were guanidinoalkanoic acid analogs made rigid by the cyclization of the guanidino group.

The inhibitors of the present invention are administered in a therapeutically effective amount, a typical human dosage of nitroarginine may range from about 0.01 mg to about 10 mg, or from about $1.4 \times 10^{-4}$ mg/kg of body weight to about $1.4 \times 10^{-1}$ mg/kg of body weight. Preferably the amount of drug which is found in the penis is less than about 200 mg/kg of penis tissue, or a local concentration of about $10^{-3}$M. More preferably the local concentration is less than about 20 mg/kg of penis tissue or about $10^{-4}$M. Even more preferred is when the concentration is less than about 2 mg/kg of penis tissue, or about $10^{-5}$M. The dosage will vary depending on the NOS inhibitor to be used and its relative potency. Dosage and length of treatment are readily determinable by the skilled practitioner.

Patches are typically made from acrylate or other polymers and may contain sufficient drug to be effective for a period of up to 1 hour. Ointments or salves are typically non-aqueous and may contain oils, fatty acids, glycerin, alcohols, etc. Aqueous solutions may also be used, if transdermal adsorption of the active ingredient is relatively fast.

According to another aspect of the invention compounds which generate NO in situ can be used to treat male impotence. Such compounds include nitroglycerin, organic nitrates, linsidomine, molsidomine, and S-nitroso-N-acetylpenicillamine. Such compounds have been known for topical application to heart tissue in both pastes and patches. These same vehicles can be applied to the penis to initiate penile erection. Intravenous administration as well as direct pharmacologic injection may also be used. Suitable dosages will generally be from about 0.01 mg to about 10 mg per application.

In another aspect of the invention nitric oxide synthase inhibitors and nitro oxide generating compounds can be applied to the urethra of those having incontinence problems or those who fail to void. Similar compositions can be used for application as are described for remedying erectile problems.

EXAMPLES

Example 1.

This example demonstrates that NOS activity is expressed in the genitourinary tract.

NO synthase activity was measured by monitoring the conversion of [$^3$H]arginine to [$^3$H]citrulline as described (Bredt, et al., *Nature* 351: 714 (1991)) on specimens obtained by anatomical dissection of adult male Sprague Dawley rats. Tissue was homogenized in 10 vol (w/v) 50 mM Tris (pH 7.4), 1 mM EDTA, 1 mM EGTA, and centrifuged at 10,000 g for 1 min at 4° C. Enzyme assays contained 25 μl of tissue supernatant and 50 μl of 100 nm [$^3$H]arginine (53 Ci/mmol; 1 Ci=37

GBq), 10 Mm NADPH and 10 Mm CaCl₂. After a 15-min incubation at room temperature, the assays were terminated with 3 ml of 20 Mm Hepes (Ph 5.5) with 2 mM EDTA and applied to 0.5 ml columns of Dowex AG50WX8 (Na+form). [³H]Citrulline was quantified by liquid scintillation spectroscopy of the 3-ml flow-through.

Several portions of the genitourinary tract displayed substantial NOS activity, monitored by the conversion of [³H]arginine to [³H]citrulline (Table 1).

TABLE 1

| Structure | [³H]Citrulline formation, (cpm/min/mg) ± SEM |
|---|---|
| Pelvic Plexus | 408 ± 36 |
| Membranous Urethra | 857 ± 105 |
| Penis | 212 ± 44 |
| Bladder | 214 ± 31 |
| Prostate | 36 ± 15 |

The data are expressed as mean values ± SEM for five experiments, normalized to cerebellar NOS activity assayed in parallel. According to the Duncan multiple range test, the amounts of NOS catalytic activity in the pelvic plexus and urethra are significantly different from the amounts in the prostate, bladder neck, and penis.

High concentrations of NOS in the pelvic plexus, referred to in the rat as the major pelvic ganglion, suggest a neuronal role for NOS. Amounts of NOS in the membranous urethra exceeded those of the pelvic plexus, and are three to four times higher than those in the penis and the bladder neck, and considerably higher than the prostate. This regional distribution of NOS activity was confirmed by Western blot analysis (not shown).

Example 2.

This example shows the results of immunohistochemical staining of rat penile tissue.

Immunohistochemistry was done as described (Bredt, et al., supra) on slide-mounted pelvic tissue sections from adult male Sprague-Dawley rats. The primary antibody was an affinity-purified NO synthase antiserum[1]

[1] Antiserum previously shown to be highly selective for NOS and to stain NOS specifically in a variety of rat peripheral tissues and in the brain (4). (1:50 dilution), which was subsequently bound with the use of an avidin-biotin-peroxidase system (Vector Laboratories) with diaminobenzidine as a chromogem. All immunohistochemical staining of NOS in penile tissues is blocked by preabsorption with recombinant NOS protein (not shown).

Figure 1B:
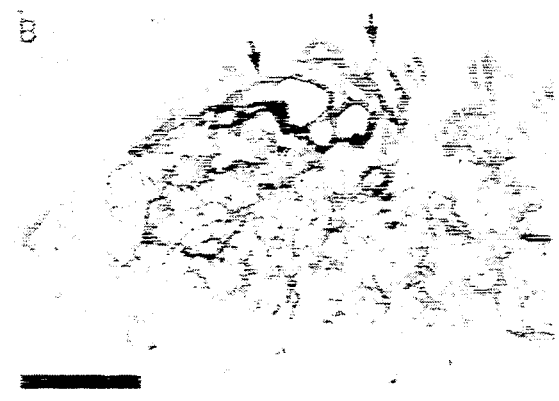
(FIG. 1B) Oblique section through the crus of the corpus cavernosum which depicts staining primarily localized to nerves in the adventitia of the deep cavernosal artery and its major tributaries (arrows) and to nerves extending into erectile tissue.

The antibody to NOS stained the pelvic plexus and its axonal processes that form the cavernous nerve (FIG. 1A), located immediately adjacent to the deep cavernosal artery, the major arterial source of the corpus cavernosum. In the proximal penis, the nerve plexus in the adventitia of the deep cavernosal arteries stained prominently, as did neuronal processes in the sinusoids and the periphery of the corpora cavernosa (FIG. 1B). This staining circumscribed the corpora cavernosa directly below their fibrous capsules, the tunica albuginea.

Figure 1C:
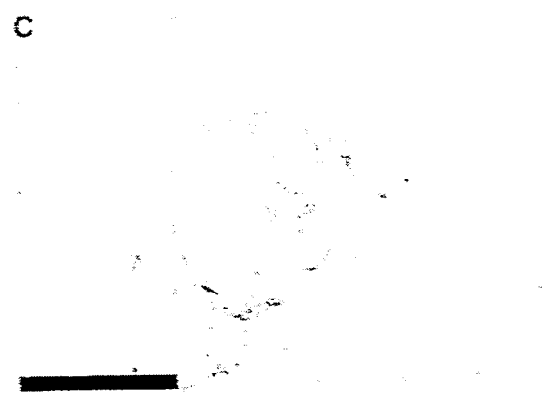
FIG. 1 shows the immunohistochemical localization of NOS in the penis.
(FIG. 1D) Coronal section through the pelvis at the level of the proximal penis which shows the corpora cavernosa merging in midline. The deep cavernosal arteries have tapered (arrows) while arterial subdivisions, the helicine arteries, have extensively arborized. The capsule containing the erectile tissue, the tunica albuginea, does not stain (arrowhead).
(FIG. 1E) Cross-section through the visible penis distally showing prominent nerve fiber staining of the dorsal penis and staining of the urethra (arrow). Bilateral cavernous spaces (CS) within the corporal bodies are shown.
(FIG. 1F) A magnified view of the dorsal penis from (FIG. 1E) showing discrete nerve fibers (NF). Staining is also localized to the adventitia (arrows) and endothelium (arrowhead) of dorsal arteries. [Scale bars.
Figure 1D:
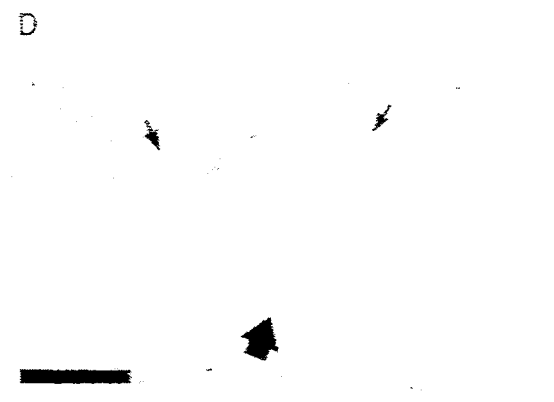
Figure 1E:
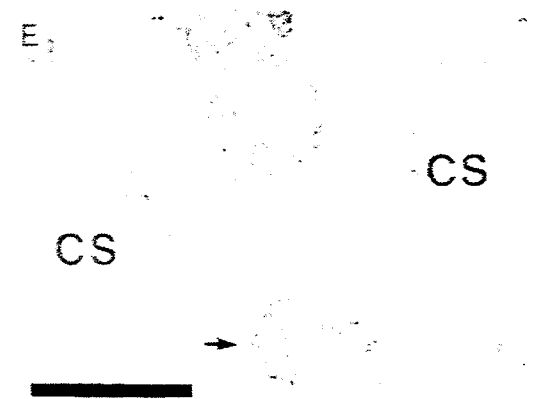
Figure 1F:
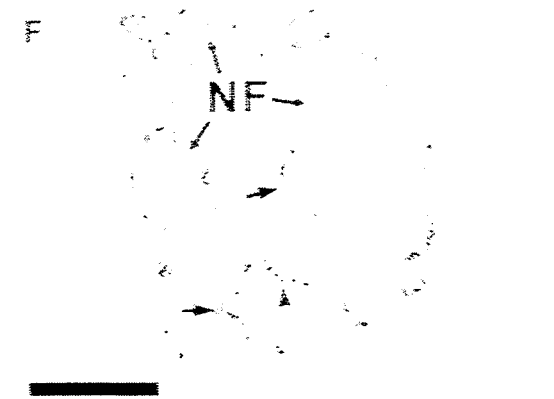

The neural specificity of NOS staining was established by bilateral cavernous nerve transection, after which we no longer observed penile neurons stained for NOS (FIG. 1C) although endothelial staining persisted (not shown). Neuronal staining of the deep cavernosal arteries continued as the arteries subdivide into the intracorporal network of helicine arteries (FIG. 1D). In the most distal portion of the corpora, staining diminished as the helicine arteries are replaced with cavernous spaces (FIG. 1E). The distal part of the penis superficial to the corpora cavernosa contained dorsal penile nerve fibers staining for NOS. (FIG. 1E and F.) Dorsal penile and cavernosal arteries stained for NOS both in their adventitial and endothelial layers; though endothelial staining was faint in the cavernosal vessels.

NOS staining in the urethra was associated with neuronal fibers coursing through the smooth muscle or the submucosal vasculature (or both) (FIG. 1E) and fits with the substantial urethral NOS catalytic activity (Table). To ensure that this distribution was not species specific, we conducted immunohistochemical localizations of NOS in the penis of dogs and demonstrated essentially identical localizations to nerve plexuses in the adventitial layer of penile arteries and the dorsal nerve of the penis.

Example 3.

This example demonstrates that inhibitors of NOS markedly diminish penile erections in vivo.

The localizations of NOS to neuronal fibers innervating blood vessels and the corpora cavernous of the penis suggested a possible role for NO as a neuronal mediator of physiologic erection. We examined this possibility in a rat model of penile erection in which we electrically stimulated the cavernous nerves of intact rats utilizing optimal parameters that evoke physiologic erection (Quinlan, et al., *J. Urol.* 141:656 (1989)).

Penile erection was induced electrically with a Grass S48 square wave stimulator in anesthetized (pentobarbital, 50 mg/kg, interperitoneally) male Sprague Dawley rats with optimal stimulation parameters (Quinlan, et al., supra). Bipolar silver wire electrodes were attached unilaterally to the cavernous nerve arising from the ipsilateral pelvic plexus situated dorsolateral to the prostate. Intracavernous pressures were measured (Gould Polygraph) with a 25-gauge needle inserted unilaterally at the base of the penis and connected to an Isotec pressure transducer. Neurostimulation was performed until a 10-sec maximal pressure recording was achieved, but no stimulation lasted longer than 90 seconds. At least 10 min elapsed between repeated stimulations. Arginine derivatives were administered into the jugular vein.

TABLE 2

| Agent | Dose (mg/kg) | % Intracavernous Pressure (± SEM) | n |
|---|---|---|---|
| L-Nitroarginine Methyl Ester | 1.0 | 75 ± 7 | 3 |
|  | 2.5 | 47 ± 5 | 10 |
|  | 5.0 | 16 ± 1 | 4 |
|  | 10.0 | 10 ± 0.3 | 3 |
|  | 40.0 | 0 | 5 |
| N-Methyl-L-Arginine | 10.0 | 63 ± 3 | 11 |
|  | 20.0 | 17 ± 2 | 2 |
|  | 40.0 | 15 ± 5 | 4 |
| N-Methyl-D-Arginine | 40.0 | 128 ± 5 | 2 |

Data represent mean values ± SEM as a percentage of the baseline pressure (range 35 to 50 mm Hg) recorded 15 min after agents were administered.

As little as 1 mg/kg of L-nitroarginine administered intravenously (i.v.) significantly reduced erection, while 2.5 mg/kg produced more than a 50% reduction. At 5 mg/kg nitroarginine almost completely inhibits erection. Intravenous bolus injections of L-arginine (25 mg/kg) partially reverse the L-nitroarginine (2.5 mg/kg) inhibition of penile erection. The physiologic L-isomer of N-methylarginine, another selective inhibitor of NOS that is less potent than L-nitroarginine, significantly inhibited penile erection at 10 mg/kg with a larger effect at 40 mg/kg. By contrast the D-isomer, which does not inhibit NOS, also failed to block erection even at 40 mg/kg. High doses of atropine (1 mg/kg i.v.) did not inhibit electrically stimulated erections. These results fit with recent experiments that show inhibition of erection by cavernosal nerve stimulation in rabbits after injections of L-nitroarginine directly into the corpus cavernosum (F. Holmquist et al., *Acta. Physiol. Scan.* 143:299 (1991). The dose required for maximal effect, about 2 mg, is effectively several hundred times greater than the parenteral doses we administered. Also, L-arginine failed to reverse effects of nitroarginine in rabbits (Holmquist, et al., Acta. Physiol. Scan. 143:299 (1991)).

DISCUSSION

The stereospecificity for inhibition of penile erection displayed by N-methylarginine as well as the very substantial potency of nitroarginine indicates that the blockade of penile erection derives from inhibition of NOS activity. This conclusion is supported by observations of some workers that relaxation of isolated corpus cavernosum muscle strips in vitro after electrical field stimulation is blocked by NOS inhibitors (R. S. Pickard, et al., *Br. J. Pharmacol.* 104:755 (1991); Ignarro, et al., *Biochem. Biophys. Res. Commun.* 170:843 (1990); N. Kim, et al., *J. Clin. Invest.* 88:112 (1991); Holmquist, et al. *Acta. Physiol. Scan.* 141:441 (1991); and Rajfer, et al., *New Eng. J. Med.* 326:90 (1992)), although other investigators report a failure of the inhibitors N-methylarginine to prevent such relaxation (Gillespie, et al., *Br. J. Pharmacol.* 97:453P (1989); Sjostrand, et al., *Acta. Physiol. Scan.* 140:297 (1990)). The selective localization of NOS in penile neurons that subserve erection as well as the ability of NOS inhibitors to block physiologic erection selectively, potently, and completely strongly implies that NO is the major if not sole neuronal mediator of erection. As in the myenteric plexus of the gastrointestinal system, NO in the penis appears to fulfill the principal criteria of a neurotransmitter. It is localized to the neurons that innervate the smooth muscle of the penis. Direct application of NO or its precursors relaxes the muscle similar to the relaxation produced by nerve stimulation (Pickard, et al., supra; Ignarro, et al., supra; Kim, et al., supra; Holmquist, et al., supra; Rajfer, et al., supra), and effects of neuronal stimulation are blocked by inhibitors of the formation of NO.

Acetylcholine is the classical neurotransmitter for the parasympathetic innervation of penile nerves responsible for erection. However, penile erection does not appear to require either cholinergic or adrenergic mechanisms (Benson, *World J. Urol.* 1:209 (1983)). VIP was advanced as a candidate transmitter for the mediation of erection based on its immunohistochemical localization in penile neurons (Polak et al., *Lancet* 2:217 (1981); Willis et al., *Life Sci.* 33:383 (1983)). However, the density of VIP-containing penile neurons in several species is substantially less than the NOS-containing neurons that we have observed in rat and dog. Injections of VIP into the penis produce some erection, but responses are relatively modest and may be elicited primarily by increasing venous outflow resistance rather than dilating penile arteries or relaxing corpora cavernosa muscle (Kiely et al, *Br. J. Urol.* 64:191 (1989); Roy et al., *J. Urol.* 143:302(1990); Juenemann et al., ibid. 138:871 (1987); Steers et al., ibid. 132:1048 (1984)). Lesion studies demonstrate that NOS-containing fibers in the adventitia of cerebral arteries arise from parasympathetic cell bodies in the sphenopalatine ganglia, many of which also contain VIP (Nozaki, et al., *J. Neurosci.*, in press). In the myenteric plexus NOS-containing neurons also contain VIP. While NOS inhibitors can almost completely block neuronally mediated gastric relaxation, antibodies to VIP can produce up to a 30% blockade of this relaxation with NOS inhibitors blocking the remaining relaxation (Li, et al., *Eur. J. Pharmacol.* 191:303 (1990)). Thus, in various portions of the parasympathetic nervous system VIP and NO might function as cotransmitters.

The immunohistochemical visualization of NOS in penile neurons clarifies functional penile innervation as described in humans by Walsh and Donker (Walsh, et al., *J. Urol.* 128:492 (1982)) and later in rat (Dail, et al., *Anat. Rec.* 224:94 (1989)). NOS-containing cavernous nerve processes penetrate the corpora cavernosa, appear to envelop the centrally situated cavernosal arteries and also extend into the corporal bodies radially and circumferentially. This implies a direct neural modulation of the vasoactivity of penile arteries, intracorporal sinusoids, and the entire tubular-shaped corpora cavernosa. Besides well characterized neuroregulation of arterial dilation in the penis, our findings suggest that penile erection also involves an active process of neurally regulated sinusoidal and corporal expansion rather than passive engorgement of cavernous spaces with blood supplied by the penile arteries.

The immunohistochemical localization of NOS in the urethra parallels its high NOS catalytic activity, suggesting a role for NO in the urethral functions regulating urinary continence or micturition.

We claim:

1. A method for treating priapism, comprising:
topically applying to an erect penis an inhibitor of NO synthase in an amount sufficient to cause said penis to become flaccid.

2. The method of claim 1 wherein the inhibitor is nitroarginine.

3. The method of claim 1 wherein the inhibitor is methyl-L-arginine.

4. The method of claim 1 wherein the inhibitor is aminoarginine.

5. The method of claim 1 wherein the inhibitor is applied intraurethrally.

6. The method of claim 1 wherein the inhibitor is applied in a patch.

7. The method of claim 1 wherein the inhibitor is applied in a salve or ointment.

8. The method of claim 1 wherein the amount of inhibitor is between about 0.01 mg and about 10 mg.

9. The method of claim 1 wherein the amount of inhibitor is between about $1.4 \times 10^{-4}$ mg/kg of body weight and about $1.4 \times 10^{-1}$ mg/kg of body weight.

10. A method for treating priapism, comprising:
administering by injection to a patient having an erect penis an inhibitor of NO synthase in an amount sufficient to cause said penis to become flaccid.

11. The method of claim 10 wherein the inhibitor is nitroarginine.

12. The method of claim 10 wherein the inhibitor is methyl-L-arginine.

13. The method of claim 10 wherein the inhibitor is aminoarginine.

14. The method of claim 10 wherein the amount of inhibitor is between about 0.0 1 mg and about 10 mg.

15. The method of claim 10 wherein the amount of inhibitor is between about $1.4 \times 10^{-4}$ mg/kg of body weight and about $1.4 \times 10^{-1}$ mg/kg of body weight.

16. The method of claim 10 wherein the administration is intravenous.

17. The method of claim 10 wherein the administration is by injection into smooth muscle innervated by penile neurons.

18. The method of claim 6 wherein the drug is nitroarginine.

19. The method of claim 6 wherein the drug is methyl-L-arginine.

20. The method of claim 6 wherein the drug is aminoarginine.

21. The method of claim 7 wherein the drug is nitroarginine.

22. The method of claim 7 wherein the drug is methyl-L-arginine.

23. The method of claim 7 wherein the drug is aminoarginine.

24. A method for treating incontinence, comprising:
applying to a urethra a compound which inhibits NO synthase in an amount sufficient to inhibit micturition.

25. The method of claim 24 wherein the inhibitory compound is nitroarginine.

26. The method of claim 24 wherein the inhibitory compound is methyl-L-arginine.

27. The method of claim 24 wherein the inhibitory compound is aminoarginine.

28. A method for treating a person who is unable to void, comprising:
applying to a urethra of a person a compound which generates NO, in an amount sufficient to initiate micturition.

29. The method of claim 28 wherein the compound is nitroglycerin.

30. The method of claim 28 wherein the compound is an organic nitrate.

31. The method of claim 28 wherein the compound is S-nitroso-N-acetylpenicillamine.

32. The method of claim 28 wherein the compound is molsidomine.

33. The method of claim 28 wherein the compound is linsidomine.

* * * * *

UNITED STATES PATENT AND TRADEMARK OFFICE
CERTIFICATE OF CORRECTION

PATENT NO. : 5,439,938
DATED : August 8, 1995
INVENTOR(S) : Soloman H. Snyder, et. al.

It is certified that error appears in the above-indentified patent and that said Letters Patent is hereby corrected as shown below:

Column 1, line 5, insert --This invention was made with government support under (USPHS grant MH-18501, DA-00266 and DK-19300, Contract DA-271-90-7408 and Research Scientist Award DA-00074, Training Grant DK-07552, Training Grant GM-07309, NIH Physician Scientist Award HL-02451) awarded by the National Institute of Health. The government has certain rights in this invention--.

Signed and Sealed this

First Day of July, 1997

*Attest:*

BRUCE LEHMAN

*Attesting Officer*   Commissioner of Patents and Trademarks